United States Patent [19]

Saxena et al.

[11] Patent Number: 5,477,000
[45] Date of Patent: Dec. 19, 1995

[54] HYPERPRODUCTION OF SHOOTS DURING A VITRO REGENERATION OF PLANT

[75] Inventors: Praveen K. Saxena, Guelph; Kamal Malik, Kitchener, both of Canada

[73] Assignee: University of Geulph, Guelph, Canada

[21] Appl. No.: 252,981

[22] Filed: Jun. 2, 1994

Related U.S. Application Data

[63] Continuation of Ser. No. 134,491, Oct. 8, 1993, abandoned, which is a continuation of Ser. No. 718,126, Jun. 20, 1991, abandoned.

[51] Int. Cl.$^6$ .............................. C12N 5/04; C12N 5/02
[52] U.S. Cl. ................ 800/200; 435/240.4; 435/240.45; 435/240.54
[58] Field of Search ........................ 435/240.4, 240.45, 435/240.54; 800/200

[56] References Cited

U.S. PATENT DOCUMENTS

| | | | |
|---|---|---|---|
| 4,354,327 | 10/1982 | Smeltzer et al. | 47/58 |
| 4,659,668 | 4/1987 | Sondahl et al. | 435/240.5 |
| 4,857,465 | 8/1989 | Barwale et al. | 403/30 |
| 4,957,866 | 9/1990 | Gupta | 435/240.4 |
| 4,992,375 | 2/1991 | Wright | 435/240.54 |

FOREIGN PATENT DOCUMENTS

| | | | |
|---|---|---|---|
| 2099851 | 12/1982 | United Kingdom | 435/240.54 |
| WO86/07378 | 12/1986 | WIPO . | |

OTHER PUBLICATIONS

Steward, F. C., et al., "Growth and Development of Cultured Plant Cells," Science, vol. 143, pp. 20–27, Jan. 1964.
Zimmerman, R. H., et al., "Tissue Culture as a Plant Production System for Horticultural Crops," Current Plant Science and Biotechology in Agriculture, Martinus Nihoff Publishers, p. 5.
Kyte, Lydiane, "An Introduction to Micropropagation", Plants From Test Tubes, Revised Edition, pp. 13, 63, 64, 67.
Cell Culture and Somatic Cell Genetics of Plants, vol. 3, "Plant Regeneration and Genetic Variability," 1986, pp. 37, 52, Edited by Vasil, I. Academic Press, Inc.
Dodds, John H. et al., "Culture of plant cells, tissues, and organs," Experiments in Plant Tissue Culture, 1982, p. 2.
Reinert, J., et al., "Isolation of Plant Material and Studies on Growth and Cell Division," Plant Cell and Tissue Culture, A Laboratory Manual, pp. 4–5.
Street, H. E., "Embryogenesis and Chemically Induced Organogenesis," Plant Cell and Tissue Culture, pp. 122–125.
Haartmann, H. T., et al., "Part IV/Aseptic Medhods of Micropropagation," Plant Propagation Principles and Practices, Fifth Edition, p. 512.
Lal, Rup, et al., "II. Culture System Steps and Methods of Shoot Induction and Profiferation," Crop Improvement Utilizing Biotechnology, pp. 73–74.
Plant Cell and Tisue Culture Principles and Applications, Edited by Sharp, W. R., et al., Ohio State University Press: Columbus, pp. 116–117.
Hussey, G., "In vitro propagation of horticultural and agricultural crops," Plant Biotechnology, Society for Experimental Biology Seminar Series 18, pp. 111–112.
Mantell, S. H. et al., Principles of Plant Biotechnology, An Introduction to Genetic Engineering in Plants, Blackwell Scientifid Publications, pp. 91–93.
Conger, B. V., Editor, Cloning Agricultural Plants Via in Vitro Techniques, 1986, pp. 6–9, 14–15, 23–50.
Communication from European Patent Office/European Search Report, Dated 30 Sep. 1992, by Examiner Dissen H.˙ D.

(List continued on next page.)

*Primary Examiner*—David M. Naff
*Assistant Examiner*—L. Blaine Lankford
*Attorney, Agent, or Firm*—Bell, Seltzer, Park & Gibson

[57] ABSTRACT

A plurality of viable plant regenerants can be produced by culturing an intact plant seed of in the presence of cytokinin and/or auxin growth factors. The growth factor is preferably benzylaminopurine and thiadiziron. The plant seed is preferably a pea, bean, geranium, peanut, grass pea, chickpea or lentil seed.

8 Claims, 1 Drawing Sheet

OTHER PUBLICATIONS

Groenwald, E. G. et al., "Callus formation and plant regeneration from seed Tissue of Aloe Pretoriensis," *Z. Pflanzenphysiologie Bd.*, 270–275 (1975).

Jackson, J. A., et al., "Rapid Multiple Shoot Production from Cotyledonary Node Explants of Pea (*Pisum Sativum L.*)," *In Vitro Cell. Dev. Biol.* 26:835–838, Aug. 1990.

HYPERPRODUCTION OF SHOOTS DURING A VITRO REGENERATION OF PLANT

This application is a continuation of application Ser. No. 08/134,491, filed Oct. 8, 1993, abandoned, which in turn is a continuation of Ser. No. 07/718,126, filed Jun. 20, 1991 abandoned.

FIELD OF THE INVENTION

This invention relates to a method for inducing direct de novo differentiation of shoots and/or somatic embryos from mature seeds leading to multiple whole plant regeneration and more particularly the development of shoots and/or somatic embryos by de novo differentiation from cells other than pre-existing maristems.

BACKGROUND OF THE INVENTION

Considerable effort has been expanded in developing ways of regenerating plants from tissue cultures. Several publications are available describing these techniques involving plant regeneration which are listed below for convenience and reference.

Barwale, U. B., Wildholm, J. M. (1989) Whole plant regeneration via organogenesis and somaclonal variation in Glycine species. U.S. Pat. No. 4,857,465;

Brown, D. C., Thrope, T. A. (1986) Plant regeneration and organogenesis. In: Cell culture and somatic cell genetics of plants, I. K. Vasil (ed), *Academic Press*, pp. 49–65;

Christianson, M. L., Warnick, D. A. (1985) Temporal requirement for phytohormone balance in the control of organogenesis in vitro. *Dev. Biol.* 112:494–497;

Douglas, G. C. (1990) Manipulation of shoot formation in cultured explants. In: Methods in molecular biology vol. 6, W. Pollard, J. M. Walker (eds). *Humana Press*, pp. 71–80;

Flick, C. A., Evans, D. A., Sharp, W. R. Organogenesis. In: Handbook of plant cell culture-Techniques and application vol. 4, *Evans MacMillan Publishing Co.*, New York, U.S.A. pp. 370–418;

George, E. F., Sherrington, P. D., (1984) Plant propagation by tissue culture, *Exegetics Ltd.* U.K., pp. 3;

Goenwald, E. G., Koeleman, A., Wessels, C. J. (1975) Callus Formation and Plant Regeneration from Seed Tissue of Aloe Pretoriensis Pole Evans. *Z. Pflanzenphysiol.* 75:270–272;

Jackson, J. A., Hobbs, S.L.A. (1990) Rapid multiple shoot production from cotyledonary node explants of pea (*Pisum sativum* L.). *In Vitro Cell Dev Biol* 26:835–838;

Skoog, F., Miller, C.O. (1957) Chemical regulation of growth and organ formation in plant tissue cultured in vitro. *Soc. Exp. Biol. Symposia* 11:118–131;

Skook, F., Miller, C. O. (1957) Chemical regulation of growth and organ formation in plant tissue culture in vitro. *Soc. Exp. Biol. Symposia* 11:118– 131;

Smeltzer, R. H. Cello, L. M. (1982) Tissue culture method for asexual propagation of pine trees and medium for use therewith. U.S. Pat. No. 4,354,327;

Vasil, I. K. (1987) Developing cell and tissue culture system for the improvement of cereal and grass crops. *J. Plant Physiol.* 128:193–218.

There are two pathways of regeneration of plants in tissue culture: Organogenesis and Somatic embryogenesis. Organogenesis is the formation of an organ, a shoot which later develops roots to produce a complete plant and visa versa. Somatic embryogenesis is the formation of somatic embryos which have both shoot and root initials and are capable of developing into whole plants (Brown and Thorpe, 1986).

The process of shoot or embryo regeneration is known to consist of two essential steps: (a) the isolation of an explant from a source seedling and (b) its culture on a nutrient medium supplemented with growth regulators (Christianson and Warnick, 1985, Douglas, 1990; Flick et al. 1983; George and Sherrington, 1984). As is appreciated, explant refers to small pieces of the seedlings cultured for inducing regeneration.

Upon culture, the explant may give rise to adventitious shoots of somatic embryos directly or may produce a mass of undifferentiated cells referred to as callus. The callus then can be made to differentiate into shoots or somatic embryos (Brown and Thorpe, 1986; George and Sherrington, 1984) by culturing on media supplemented with growth regulators.

The discovery of the principle of regeneration in tissue cultures was made in 1957 by Skoog and Miller. It was suggested that all types of cell growth and differentiation from tissue/callus cultures is controlled by the balance of auxins and cytokinins in the medium. The theory has been found to be true in hundreds of studies subsequently conducted by many researches (Flick et al. 1983; George and Sherrington, 1984).

Consequently, it is now well established that an explant can be made to differentiate into shoots or somatic embryos by minor variations in hormonal balance and source of explants. For instance in pea, there are several reports describing somatic embryogenesis and shoot regeneration (Tetu, T., Sanywan, R. S., and Sangwan-Neyyeal, B. S., Direct Somatic Embryogenesis and Organogenesis in Cultured Immature Zygotic Embryos of *Pisum sativum* L., *J. Plant Physiol.* 137:102–109, 1990).

In many instances for example geranium (Wilson, Qureshi and Saxena, 1990, Unpublished), lentil, beans, carrot (Malik and Saxena unpublished) somatic embryos are discernable for a very brief period and the end products are shoots. Since the fate of cell to produce somatic embryo or shoot is governed by hormonal balance and this said balance is influenced by a variety of factors, such as type of explant, culture medium, temperature and light, the possibility of the development of either a shoot or an embryo independently or simultaneously is very strong. Simultaneous occurrence of shoot and somatic embryos was seen in many cultures in our experiments (e.g., in *Arachis hypogea, Phaseolus coccenius, P. wrightii, Pelargonium hortorun*). For the purpose of multiple plant regeneration, the subject of this invention, it is not important if the end products, the shoots, are developed from structures which started as a shoot or as an embryo, but later developed into shoots. Therefore, the term regenerants shall be used hereafter to describe the regenerated plants. Regenerants (Ro) is a commonly used term to describe the regenerated plants of tissue culture original [Maclean, P. and Grafton, K. F., Regeneration f Dry Bean (*Phaseolus volgaris* L.) via Organogenesis, *Plant Science*, 6:117 (1989); Franklin, C. I., Trieu, T. N., Gonzales, R. A., Dixon, R. A., Plant Regeneration from Seedling Explant of Green Beans (*Phaseolus vulgaris* L.) via Organogenesis, *Plant Cell Tissue and Organ Culture* 24:199–206 (1991)] irrespective of their origin as a shoot or an embryo.

The success in regenerating plants from a wide variety of species via organogenesis or somatic embryogenesis in plant tissue cultures by manipulating quantitative interaction of phytohormones has resulted in a definite pattern of experimental approach to achieve regeneration. The procedure involves preparation of explants from seedlings raised from a seed (stage I), culture of explants (stage II), and incubation to allow growth and differentiation (stage III) as shown in Flow Chart 1.

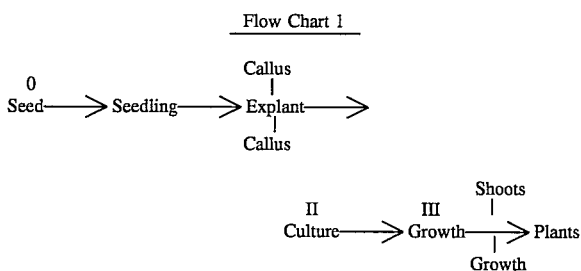

There seems to be a consensus that the success in inducing regeneration depends upon the choice of the explant and the nutritional and physical milieus of explant culture (Brown and Thorpe, 1986). Thus, a great deal of research has been directed towards the optimization of physiological conditions of the source seedlings, selection and culture of explants, and the phytohormones used to initiate tissue cultures (stages I, II, and III in Chart 1). The see (stage 0 in Chart 1) has also been used as an explant but prior to culture it was cut into smaller segments (Groenwald et al., 1975).

However, whole embryos separated mechanically from the seed have been used quite successfully in many plants including cereals and legumes (U.S. Pat. No. 4,857,465 and Vasil, 1987). For example, Barwale et al. (1989) isolated young embryos to develop regenerating callus cultures of soybean (U.S. Pat. No. 4,857,465).

In one previous development, Smeltzer et al. (1982) used nuclear tissue from seeds to obtain multiple shoots (U.S. Pat. No. 4,354,327). Smeltzer et al. provided a method for recovering multiple shoot buds capable of forming plants. As many as ten regenerants from one seed, was described by Smeltzer et al. However, the data given therein showed only percentages of seeds giving buds in response to a particular treatment; it was not clear if all treatments produced two or in between two and ten buds per seed. In addition, a maximum of four germinating seeds were used to estimate the percent seed with buds. The procedure of Smeltzer et al. essentially comprises stimulation of seed germination followed by surface serialization and culture in a nutrient medium containing BAP and abscisic acid (ABA). The method of stimulation of seed involved making a rook end or micropylar cut into the endosperm of the seed and then immersing the seed in a 1% hydrogen peroxide solution for one week. Thereafter, seed coat was removed with a thumbnail and isolated nucellar tissue was surface sterilized before inserting the protruding root radicle into culture medium. Such removal of seed coat following a cut into the endosperm results in injury to the seed tissue, but for purposes of their technique such injury is not critical.

Our discovery involves the use of whole, completely intact seeds where, during culture thereof, the intactness of the seedling derived from the cultured seed is maintained. The term intack implies that the seed is physically uninjured, ungerminated and viable for purposes of culture in developing a seeding bearing differentiated regenerants.

SUMMARY OF THE INVENTION

According to an aspect of the invention, a process is provided for producing a plurality of viable plant regenerants from a single intact plant seed. The process comprises:
i) culturing an intact, normally healthy plant seed in a suitable medium, said seed being free of contaminants to said medium,
ii) providing in said medium a growth regulator of sufficient concentration to promote a first growth phase where at least one shoot is formed from said seed and subsequently induce a second growth phase in which de novo differentiation in said at least one shoot produces said plurality of regenerants,
iii) continuing culture of said seed during said second growth phase until said regenerants are distinct and well formed.

According to another aspect of the invention, the process for producing the plurality of viable plant regenerants further comprises the steps of:
iv) harvesting said distinct and well formed regenerants;
v) transferring said harvested regenerants to a culture medium which promotes root development;
vi) culturing said transferred regenerants to produce therefrom, seedlings.

According to another aspect of the invention, the process further comprises the steps of:
i) harvesting said distinct and well formed regenerants;
ii) separating said harvested regenerants;
iii) storing said separated regenerants for subsequent use in developing seedlings therefrom.

According to another aspect of the invention, plant regenerants as isolated from differentiated de novo growth of a cultured seed of this invention is provided.

According to another aspect of the invention, a plant seedling grown from de novo differentiated regenerants derived from tissue prepared by the process of this invention is provided.

BRIEF DESCRIPTION OF THE DRAWINGS

Preferred embodiments of the invention are demonstrated with respect to the drawings wherein.

DETAILED DESCRIPTION OF THE PREFERRED EMBODIMENTS

Figure 1:
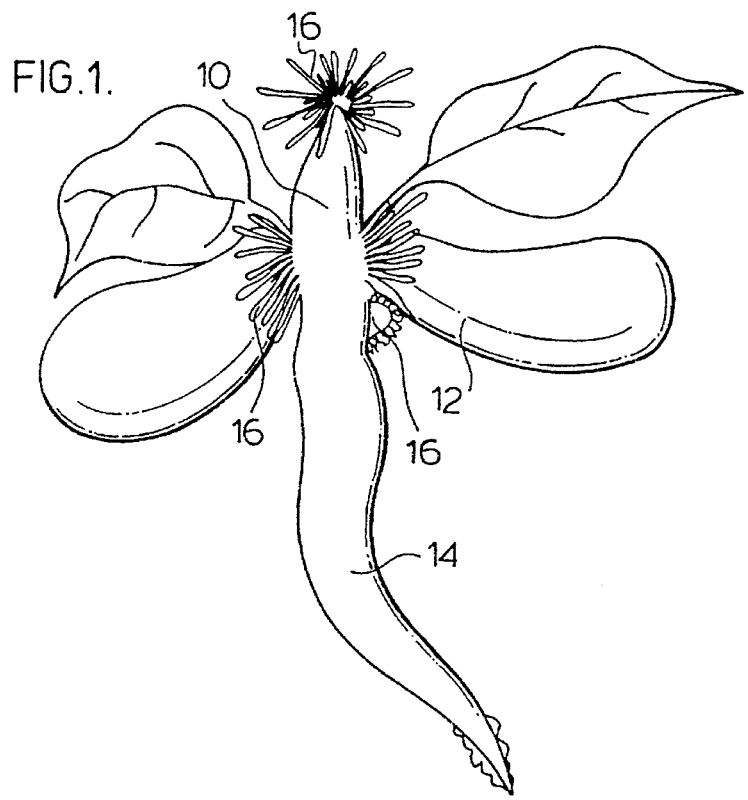
FIG. 1 is a sketch showing de novo regenerant from the pi Phaseolus vulgarisshoots in the region of the double arrow.

The principles of the invention are demonstrated in accordance with the following preferred embodiments of the invention.

From the discussion of prior techniques, it is generally accepted that explant preparation is the first step to be followed in regenerating plants in tissue culture. The isolation of the explant material with subsequent tissue culture results in the development of multiple shoots which can be segregated and grown into seedlings. As already discussed, several procedures have been developed for suitable explant preparation. Once the necessary growth from the cultured seed is provided, the explant material is removed and the seed discarded. Quite surprisingly, with the process of this invention, avoidance of the step in producing the explant material, yet with continued culture, in suitable concentration of growth regulators, produces de novo plurality of regenerants the number of which is significant, and in some instances, 10 to 20 fold greater than what can be obtained with the explant procedure. This result is quite surprising and hence very significant from the standpoint of development of multiple seedlings from a single seed. Mass propagation of ornamental, vegetable and other plant varieties, as well as, selection of new varieties can now be expedited, as well as expedition of the selection of mutants and transgenic plants.

The process according to this invention which provides direct differentiation from the cultured seed also offers many advantages from the standpoint of an experimental system in the study of biochemical and molecular events in organ determination and the development and the mechanism of action of growth hormones, because a rapid differentiation of de novo material is provided. The high frequency of direct shoot morphogenesis facilitates mutant selection as well as genetic transformation of various plants.

Our discovery preferably involves the use of the whole, completely intact, physically uninjured and ungerminated seed and the maintenance during continued culture of the intactness of the seedling derived from the cultured seeds.

The method of this invention for inducing a high frequency of direct de novo regenerants leads to whole plant development where the de novo regenerants are from tissues other than preexisting maristems. We have found, contrary to the popular notion, that the conventional excise of explant preparation is not essential for the induction of regenerant production. Direct culture of seeds, in the presence of commonly used growth regulators can stimulate a high frequency of direct differentiation of regenerants and the technique per se can be applied successfully to a wide variety of plant species. The procedure is based on a novel approach of bypassing the conventional step of explant preparation and shifting the focus of attention on the manipulation of the seed. The novel regeneration scheme is outlines in Flow Chart 2:

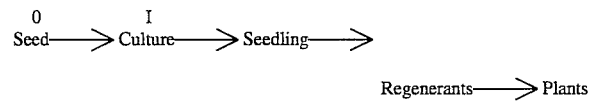

Flow Chart 2.

The procedure of seed culture is a one-step, easy to perform method due to the riddance of the prior excision or explant preparation step, by virtue of the differentiation of shoots or somatic embryos occurring on an intact seedling. This new procedure reduces the number of culture manipulations to only one. The single step required to initiate and complete the induction of shoots or somatic embryos in the placement of sterilized seeds on to a culture medium containing well known plant growth regulators.

The method and product of this invention is applicable to a variety of plants which include legumes, ornamentals, vegetables, grains, trees, and ornamental shrubs.

The process of this invention is directed to de novo differentiation from plants cells, other than preexisting maristems, of the original single shoot of the germinated seed. Normally, the necessary explant material is derived from the maristems for purposes of duplication or multiplication of the plant. Instead, the process of this invention uses sufficient concentration of growth regulators to provide culture conditions which stimulate or activate de novo differentiation of regenerants in the growing shoot or shoots from the seed. It is important that the seed be intact, that is, the seed cannot be cut into pieces or, in any other way, injured before culture. The intact seed must be healthy, that is not wrinkled or other signs of degradation. The seed coating is preferably intact and not in any way punctured which could impart on its subsequent activity to promote de novo growth when in the correct concentration of growth regulators during culture. It is thought that the culture of intact seeds in suitable concentration of growth regulator, results in the embryo cells being programmed to produce regenerants, which keep on dividing and get distributed over the body of the plant shoot. It is theorized that these programmed cells produce regenerants when the suitable environment, that is the correct concentration of growth regulators is in the medium. It is theorized that any cutting or other injury to the seed may, in some way, destroy these embryonal cells or effect their ability to induce de novo regenerative growth during continued culture in sufficient concentration of growth regulators.

Another significant advantage of this invention is not having to alter or cut the seed is to reduce labour and development of mechanical apparatus to handle the seed during initial culture of the system. The seed can be placed in the culture medium for purposes of regeneration which can translate into considerable savings in time, labour and overall costs of production. This feature, in combination with the significant outcrop of 10 to 20 fold greater number of regenerants, provides a significant increase in processing efficiency to prepare plants from a single seed.

The process according to an aspect of this invention is capable of providing a plurality of viable plant regenerants from a single intact plant seed. Such process totally avoids the step of developing explant material which in the past was subsequently cultured to yield very low numbers of multiple regenerants. Instead, the process of this invention cultures the intact normally healthy pant seed in a suitable medium. As already explained, by intact it is meant that the seed is whole and by normally healthy it is meant that the seed is able to produce at least a single shoot when cultured in the medium. The seed is prepared in a manner so as to be free of contaminants to the medium so that other microorganism potentially harmful to the process do not exist in the medium.

With reference to FIG. 1, the growth regulator used in the medium is of a sufficient concentration to promote the growth of one or more shoots 10 from the seed 12 with a root portion 14. This may be referred to as the first growth phase of the process. In the prior art procedure, once the one or more shoots is formed, the explant material is derived from such shoots. However, with the process of this invention, culture of the seed is continued. By virtue of the growth regulator being present in the medium at sufficient concentration, the growth induces a second growth phase during which there is de novo differentiation in one or more shoots and produces a plurality of regenerants 16. Culture of the seed with the plurality of regenerants 16 is continued during the second growth phase until the regenerant 16 are distinct and well formed to permit harvesting thereof from the original seed 12. The growth regulator is therefor present in the medium in a concentration in excess of the normal concentration of growth regulator required to promote shoot development during the first phase of growth. By promoting the development of de novo differentiation, the distinct and well formed regenerants may be harvested and transferred to a cultured medium which promotes root development. Culturing of the harvested regenerants is continued to produce seedlings therefrom.

Alternatively, the harvested regenerants in the form of shoots and/or embryos may be stored in a suitable environment for subsequent use.

To ensure that the seed to be cultured is free of contaminants to the medium the seed may be sterilized, that is surfaced sterilized before use. A variety of sterilizing techniques are well known in the art for purposes of preparing seeds for culture. Such sterilizing techniques included contacting the seed with a sterilizing solution which includes at least one sterilizing agent. Suitable sterilizing agents include, sodium hypochlorite, calcium hypochlorite, mercuric chloride, ethyl alcohol and sulfuric acid.

The culture medium contains suitable, well known additives as well as growth regulators. The basic composition of the medium may be i) salts or Murashige and Skoog at half to full strength
ii) vitamins of B5
iii) sucrose at 1 to 6%
iv) Gelrite at 0.2 to 0.5% (w/v) or Agar 0.6 to 1.2% (w/v).

The growth regulators may be selected from several known growth regulators, all of which have the ability to promote shoot development. The groups of growth regulators may be categorized as follows:

i) natural and synthetic cytokinins
ii) natural and synthetic auxins
iii) cytokionin-active urea derivatives The natural and synthetic cytokinins may be selected from the group consisting of BAP, kinetin, zeatin, and $N^6$-substituted derivatives.

Natural and synthetic auxins may be selected from the group consisting of IAA, NAA, 2,4-D, IBA and their derivatives.

Cytocykionin-active urea derivatives may be selected from the group consisting of thiadiziron, diphenylurea, N-phenyl-N'-(4-pyridyl)urea and their derivatives.

It is appreciated that the growth regulators used in the medium may be one or more components selected from any one group or components mixed and selected from two or more of the above listed groups. Depending upon the type of growth regulator used, the concentration thereof will usually range up to 100 μM with a preferred range of 5 to 80 μM. It has been found that with most growth regulators an amount less than 5 μM is not sufficient to induce the de novo differentiation of regenerants.

Based on the theory that certain calls are activated during the preliminary or first phase of growth and which subsequently cause de novo differentiation, may explain whey there are several variations in the pattern of regenerant differentiation in various plants. With Epigeal type plants, cotyledons emerge out and remain attached to main shoots. Whereas with hypogeal type plants cotyledons remain underground and only the epicotyledon comes out. With epigeal germination, only one shoot is seen and more shoots develop de novo from various parts of this shoot such as around noes, apex base of the cotyledon and the cotyledon itself, that is, wherever the optimal hormonal balance of the growth regulators becomes available in the plant. In hypogeal type germination, the epicotyl first develops several epicotyls. The de novo growth occurs with new regenerants occurring on these multiple epicotyls.

Preferred growth regulators are BAP and/or thidiazuran (TDZ). TDZ has several homologous compounds, some of which work as well as TDZ, it therefore being understood that compounds which have the same effect as the itemized growth regulators are encompassed by this invention. TDZ not only acts as a growth regulator but also has the advantage of inducing synthesis and/or accumulation of other growth regulators. Regeneration by somatic embryogenesis in many plants can be induced by TDZ during prolonged culture. It is likely that TDZ affects auxins as well as cytokinins. The use of BAP or TDZ together or the use of an auxin and BAP or an auxin and TDZ are effective as well. In tissue cultures of some cereals, carrot and fodder crops an auxin (2,4-D) alone induces somatic embryogenesis and in some conifers, legumes and asters BAP will work more than adequately. The significant aspect in the use of the growth regulators is the induction or morphogenesis in the cells of the seed embryo, which although commonly achieved by the addition of growth regulators, it is appreciated that external factors as well may induce morphogenesis such as heat, electric current and the like.

A preferred embodiment for seed culture consists of only one step: culture of surface sterilized seeds on the induction medium. Surface sterilization of seeds is achieved by known procedures. Seeds can be surface sterilized by immersion first in 95% ethanol for about one minute and then in a solution of a commercial bleach (0.5–2% sodium hypochlorite) containing a few drops of the surfactant "Tween 20"® for 10 min. The sterilant is replaced with a fresh solution of the same composition after 10 min and the contents stirred continuously after 10 min and the contents stirred continuously for another 10 min using a magnetic stirrer. The seeds are then washed thoroughly with deionized sterile water (5–6 times, each wash 100 ml) and only healthy, unwrinkled seeds are used for in vitro germination. For seeds with thick seed coat for example, certain large-seeded legumes, a brief treatment of about one minute in concentrated sulfuric or hydrochloric acid followed by two quick rinses in sterile water can increase the efficiency of sterilization with sodium hypochlorite.

About 5–9 sterile seeds can be placed into each of the 300 ml Magenta boxes (Magenta Corporation, Chicago, Il., USA) containing 45 ml of the culture medium. The basic culture medium used contains salts of Murashige and Skoog (1962), vitamins of B5 (Gamborg et al. 1968), 3% sucrose and 0.25% Gelrite (Scott Laboratories, Carson, Ca., U.S.A.) (Table 1).

Growth regulators are added to the basic medium at 1 to 80 μM concentrations. All media were adjusted to pH 5.7 prior to autoclaving at 0.122 MPa for 20 min.

Cultures are incubated at 24° C. in darkness for initial two weeks and later transferred to light (20–50 umol $m^{-2}$ $s^{-1}$; 16 h photoperiod) omitted from "cool white" fluorescent tubes. For incubation in darkness, the culture boxes were wrapped in aluminum foil. Cultures of some plants may be kept in light from the beginning.

TABLE 1

The composition of the nutrient medium containing salts of MS (Murashige and Skoog, 1962) medium and vitamins according to Gamborg at al. (1968).

| Compound | Concentration (mg/liter) |
|---|---|
| $NH_4NO_3$ | 1650 |
| $KNO_3$ | 1900 |
| $MgSO_4.7H_2O$ | 370 |
| $MnSO_4.H_2O$ | 169 |
| $ZNSO_4.7H_2O$ | 8.6 |
| $CuSO_4.5H_2O$ | 0.025 |
| $CaCl_2.2H_2O$ | 440 |
| KI | 83 |
| $CoCl_2.H_2O$ | 0.025 |
| $KH_2PO_4$ | 170 |
| $H_3BO_3$ | 6.2 |
| $Na_2MoO_4.2H_2O$ | 0.25 |
| $FeSO_4.7H_2O$ | 27.85 |
| $Na_2EDTA$ | 37.3 |
| Myolnositol | 100.0 |
| Nicotinic acid | 1.0 |
| Thiamin HCl | 10.0 |
| Sucrose | 3000.0 |
| Pyridoxine HCl | 1.0 |

TABLE 1-continued

The composition of the nutrient medium
containing salts of MS (Murashige and Skoog, 1962) medium
and vitamins according to Gamborg at al. (1968).

| Compound | Concentration (mg/liter) |
| --- | --- |
| pH = 5.7 | |

EXAMPLE 1

Phaseolus vulgaris L.

Common bean (*Phaseolus vulgaris*), a known refractory species to regenerate in vitro, was chosen as the experimental system to test the efficacy of seed culture method. Benzylaminopurine (BAP), a potent cytokinin commonly used for shoot initiation, was used as the chemical stimulus for inducing the seeds. Germination of seeds occurred in seven to nine days on basal and BAP-supplemented media of Table 1 with a germination frequency of about 80 to 90%. In absence of BAP or in the presence of a low concentration, i.e.: in the range of 5 µM, seeds developed single shoots with a normal pair of leaves; two shoots developed from the buds in the axils of cotyledonary nodes. Interestingly, however, on a medium containing a high concentration BAP (50 µM), several regenerants were seen to emerge after two weeks of culture from the tissue surrounding the axillary shoots and after one more week there seemed to be an outburst of regenerants. Similarly, numerous regenerants differentiated around the periphery of apical bud. Although, more than 200 young regenerants were seen to have developed from one axil or apex, only those regenerants which were well-formed and were capable of developing into whole plants were counted and included in Table 2. A substituted urea which has cytokinin-like activity was also very effective in inducing regeneration and at a relatively lower concentration of 10 µM (Table 2).

TABLE 2

The differentiation of shoots from seeds of
*Phascolus vulgaris* in the presence of BAP and TDZ.

| Concentration | No. of de novo shoots per axil or apex | |
| --- | --- | --- |
| (µM) | BAP | TDZ |
| 0 | 0 | 0 |
| 10 | 0 | 60 |
| 20 | 10 | 60 |
| 40 | 32 | 50 |
| 60 | 46 | 30 |
| 80 | 62 | 20 |

TDZ has more effective high BAP not only in use of low concentration but in duration as well. Culture of seeds for 2 weeks in presence of TDZ (10 µM) induced regeneration excess after transfer of seeds to minus TDZ.

EXAMPLE 2

Pisum sativum Medium

Figure 2:
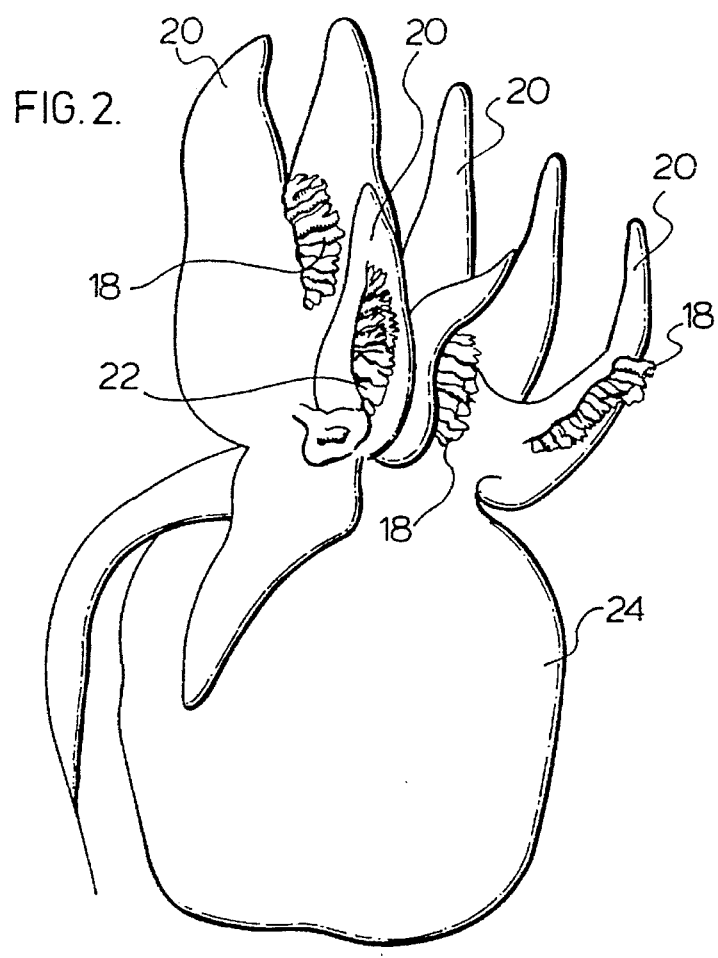
FIG. 2 shows multiple regions of de novo regenerants in *Pisum sativum.*

Germination of seeds occurred after three to four days of culture. Approximately, 80–95% seeds germinated in all experiments, irrespective of the presence or absence of BAP in the culture medium. Seeds, cultured on MS medium lacking BAP, produced single shoots with well formed roots. By contrast, seeds cultured on media containing 10–50 µM BAP produced multiple shoots, (epicotyls) but did not develop roots, although a limited growth of the radicle was observed. The percentage of seeds with multiple epicotyls after two weeks of culture ranged between 80–90%, and the number of multiple epicotyls per responding seed varied between 5 and 10. On media containing lower concentrations of BAP, 1 to 5 µM only one shoot was obtained from each germination seed. A prolonged culture (three to six weeks) of seeds in the presence of 25 to 50 µM BAP resulted, as shown in FIG. 2, in de novo differentiation of numerous regenerants 18 from the advantitious epicotyls 20 branching from the seed 24. The epidermic of one or more of the epicotyls 20 appeared to split apart lengthwise, for example at 22, and regenerants differentiated across the crevis-like opening 22 from subepidermal region. The de novo differentiation of regenerants occurred without any callus formation and optimum response was induced by 25 and 50 µM BAP (Table 3). About 80–85% of seed which had multiple shoots showed de novo differentiation of regenerants. Regenerants appeared differentiated from cell layers just below the epidermis. Although, approximately 150–300 de novo differentiated shoot buds (from first formed adventitious multiple shoots) per seed were counted, the average number of buds which appeared to be well formed and elongated more than 1 cm was 90 (Table 3). TDZ was equally effective (Table 3). These harvested buds were able to form roots on a medium containing 2.5 µM NAA and resulting plantlets could be transplanted to soil.

TABLE 3

The effect of 6-benzylaminopurine (BAP on de
nova differentiated ragenerants in seeds cultures of
*Pisum sativum*. (—) denotes tha absence of shoot bud
differentiation.

| | De novo regenerants | |
| --- | --- | --- |
| Concentration | BAP | TDZ |
| 0 | — | — |
| 5 µM | — | — |
| 10 µM | 24 | 20 |
| 20 µM | 24 | 22 |
| 50 µM | 60 | 135 |
| 80 µM | 90 | 120 |

EXAMPLE 3

Arachis hypogea

In culture of peanut (*Arachis hypogea*) seeds, which germinate like bean seeds, another variation in the pattern of shoot differentiation was observed: the differentiation of shoot buds occurred from cotyledonary tissue, initiating from the proximal end attached to the shoot and later spreading all over the surface.

EXAMPLE 4

Pelargonium bortorum (geranium)

In plants with smaller seeds like geranium and carrots differentiation of shoots or somatic embryos occurred from areas just below the apex or from hypocotyl region.

OTHER EXAMPLES

Table 4 shows the plant species in which direct differentiation of regenerants was achieved by seed culture on nutrient medium (Table 1) enriched with a cytokinin, preferably 6-benzylaminopurine (0 to 80 μM) or Kinetin (0 to 80 μM), or cytokinin like compound, thiadizuron (1 to 80 μM), used alone or in combination with an auxin preferably indoleacetic acid (0 to 50 μM) or naphthaleneacetic acid (0 to 50 μM). The pattern of the development of regenerants was similar to that described in many species. In our experience, the differentiation of cells into regenerants can be influenced with minor variations in types and concentrations of growth regulators. In some examples such as *Phaseolus coccenius*, differentiation of shoots and somatic embryos was observed at two different loci of the same seedling. The de novo differentiation of regenerants was achieved in a wide variety of plants under similar culture conditions suggests the general applicability of this method. The detailed histological examination revealed that de novo differentiation occurred from subepidermal layers of cells. In all cases cited herein, whole plants were recovered from de novo differentiating structures (regenerants) using standard methods of root development known to the art. As many as 160 plants per seed were regenerated from one seed (Table 3). A seedling was cultured further, after the removal of first formed regenerants, on a medium similar to the one used originally, for producing more regenerants.

TABLE 4

The Lint of species in which de novo differentiation of ragenerants was achieved by whole seed culture method and plants were regenerated from differentiated structures.

| Plant species | No. of plants per seed |
| --- | --- |
| *Arachis hypagea* | ++++ |
| *Cicer arietinum* | ++++ |
| *Daucus carota* | ++ |
| *Glycine max* | ++ |
| *Lathyrus cicera* | ++++ |
| *Lathyrus latifolius* | +++ |
| *Lathyrus ochrus* | +++ |
| *Lathyrus sativus* | ++++ |
| *Lens culinaris* var Laird | ++++ |
| *Lens culinaris* var Indian Head | ++++ |
| *Lens culinaris* var Eston | ++++ |
| *Lens ervoides* | +++ |
| *Pelargonium x hortorum* | +++ |
| *Phaseolus vulgaris* var Fiesta | ++ |
| *Phaseolus vulgaris* var Kinghorn | ++++ |
| *Phaseolus vulgaris* var Mayflower | +++ |
| *Phaseolue vulgaris* var Montcalm | ++++ |
| *Phaseolus vulgaris* var Revolution | +++ |
| *Phaseolus vulgarin* var Sprint | ++ |
| *Phaseolus coccineus* | ++++ |
| *Phaseolus wrightii* | ++++ |
| *Phaseolus lunatus* | +++ |
| *Pisum sativum* var Century | ++ |
| *Pisum sativum* var Dwarf Grey Sugar | ++ |
| *Pisum sativum* var Early Frost | + |
| *Pisum sativum* var Green Arrow | ++ |
| *Pisum sativum* var Honey Pod | ++ |
| *Pisum sativum* var Laxton Progress | ++++ |
| *Pisum sativum* var Lincoln | ++ |
| *Pisum sativum* var Little Marvel | ++ |
| *Pisum sativum* var Lucy Lady | +++ |
| *Pisum sativum* var Novella | + |
| *Pisum sativum* var Olympia | ++ |
| *Pisum mativum* var Oregon Sugar Pod II | ++ |
| *Pisum sativum* var Patriot | ++ |
| *Pisum sativum* var Peter Pan | ++ |
| *Pisum sativum* var Spring | ++ |
| *Pisum sativum* var Sugar Snap | + |

TABLE 4-continued

The Lint of species in which de novo differentiation of ragenerants was achieved by whole seed culture method and plants were regenerated from differentiated structures.

| Plant species | No. of plants per seed |
| --- | --- |
| *Pisum sativum* var Tall Telephone | ++ |
| *Pisum sativum* var Titan | ++ |
| *Pisum sativum* var Trapper | ++ |
| *Pisum sativum* var Triplet | ++ |
| *Vicia faba* | ++ |
| *Vigna aconitifolius* | +++ |
| *Vigna mungo* | ++ |
| *Vigna radiata* | ++ |

+ = 10–50; ++ = 50–60; +++ = 60–100; ++++ = 100–160

The regenerants may be stored until used or shipped. For storage purposes, regenerants may be transferred to a medium containing half of the normal strength of culture medium and maintaining at a relatively lower temperature of 18° to 20° C. compared to 24° to 28° C. used normally.

As is appreciated with any of the above examples, the de novo formation of regenerants may be harvested and placed in a root forming medium to develop seedlings, such mediums are readily available. A preferred medium is of the following type having the following general grouping of constituents:
1. salts of MS half to full strength;
2. vitamin B5;
3. sucrose 1 to 3%
4. Gelrite 0.25 to 0.3% (w/v) of Agar 0.6 to 1.2% (w/v)
5. Auxim (IAA, NAA or IBA 0.1 to 50 μM)

In accordance with the various aspects of this invention, an easy, efficient and rapid method is provided for inducing a high frequency of direct differentiation of regenerants and plant regeneration from several types of seeds. Contrary to popular belief, the isolation of explant is not necessary to induce shoot regeneration. The process of this invention provides the direct differentiation of shoots and/or somatic embryos to offer the many advantages as previously described. The rapidity and high frequency of direct shoot morphogenesis, routinely obtainable in seeds cultures, is expected to facilitate genetic transformation of a variety of plants. Such genetic transformation can be accomplished with use of *agrobacterium, tumefaciens* for example and biolistic microprojectiles. An additional advantage of seed culture is the riddance of excision or the explant step as the differentiation occurs on the intact seedling which reduces the number of culture manipulations to only one.

Although preferred embodiments of the invention are described herein in detail, it will be understood by those skilled in the art that variations may be made thereto without departing from the spirit of the invention or the scope of the appended claims.

We claim:

1. A process for producing a plurality of viable plant regenerants, said plurality in excess of 14, from a single intact plant seed, said plant seed being selected from the group consisting of seeds for pea, bean, geranium, peanut, grass pea, chickpea and lentil, said process comprising:

(i) culturing an intact plant seed under aseptic conditions in a suitable culture medium comprising a growth regulator selected from the group consisting of benzylaminopurine and thiadiziron wherein said growth regulator is present in a concentration in the amount of about 10–100 μM; and (ii) continuing said culturing of the seed until said in excess of 14 regenerants are distinct and well formed.

2. A process of claim 1 further comprising sterilizing said intact plant seed prior to culturing in said medium.

3. A process of claim 2 wherein said sterilization of said intact plant seed comprises contacting said seed with a sterilizing solution, said sterilizing solution including at least one sterilizing agent selected from the group consisting of sodium hypochlorite, calcium hypochlorite, mercuric chloride and ethyl alcohol.

4. A process of claim 1 wherein said medium comprises in addition to said growth regulators, one or more components selected from the group consisting of:

i) salts of Murashige and Skoog half to full strength,
ii) vitamin B5,
iii) sucrose—1 to 3%,
iv) Gelrite—0.2 to 0.5% weight/volume and
v) Agar 0.6 to 1.2% weight/volume.

5. A process of claim 4 wherein said intact plant seed is cultured under alternating periods of light and dark.

6. A process of claim 1 further comprising the steps of:

(iii) harvesting said regenerants;

(iv) transferring said harvested regenerants to a culture medium which promotes root development; and (v) culturing said transferred regenerants to produce seedlings.

7. A process according to claim 1 further comprising the steps of iii) harvesting said plurality of regenerants, iv) separating said harvested regenerants into individual regenerants; and v) storing said individual regenerants in a suitable vehicle for subsequent use in developing seedlings therefrom.

8. A process of claim 1 wherein said medium is adjusted to a pH of 5.7.

* * * * *

UNITED STATES PATENT AND TRADEMARK OFFICE
CERTIFICATE OF CORRECTION

PATENT NO. : 5,477,000  Page 1 of 2
DATED : December 19, 1995
INVENTOR(S) : Praveen K. Saxena and Kamal Malik It is certified that error appears in the above-identified patent and that said Letters Patent is hereby corrected as shown below:

Column 1, Line 54, delete "Skook, F., Miller, C. O. (1957) Chemical regulation of growth and organ formation in plant tissue culture in vitro. *Soc. Exp. Biol. Symposia* 11:118 -131;"

Column 2, Line 30, delete "Sanywan" and insert --Sangwan--.

Column 2, Line 38, delete "cell" and insert --cells--.

Column 2, Line 46, delete "*hortorun*" and insert --*hortorum*--.

Column 2, Line 53, delete "original" and insert --origin--.

Column 2, Line 54, delete "f" and insert --of--.

Column 2, Line 55, delete "*volgaris*" and insert --*vulgaris*--.

Column 2, Line 65, delete "achieve" and insert --achieved--.

Column 3, Line 22, delete "see" and insert --seed--.

Column 3, Line 32, delete "nuclear" and insert --nucellar--.

Column 3, Line 45, delete "rook" and insert --root--.

Column 4, Line 36, delete "pi".

Column 4, Line 36, insert a space between vulgaris and shoots.

UNITED STATES PATENT AND TRADEMARK OFFICE
CERTIFICATE OF CORRECTION

PATENT NO. : 5,477,000  
DATED : December 19, 1995  
INVENTOR(S) : Praveen K. Saxena and Kamal Malik Page 2 of 2

It is certified that error appears in the above-identified patent and that said Letters Patent is hereby corrected as shown below:

Column 5, Line 30, delete "outlines" and insert --outlined--.

Column 5, Line 53, delete "plants" and insert --plant--.

Column 6, Line 29, delete "pant" and insert --plant--.

Column 6, Line 34, delete "microorganism" and insert --microorganisms--.

Column 7, Line 39, delete "calls" and insert --cells--.

Column 8, Line 58, delete "CoCl$_2$.H$_2$O" and insert --CoCl$_2$-2H$_2$O--.

Column 10, Line 41, after 10µM, delete "24" and insert --15--.

Column 11, Line 36, delete "*hypagea*" and insert --*hypogea*--.

Signed and Sealed this

Second Day of July, 1996

Attest:

BRUCE LEHMAN

Attesting Officer

Commissioner of Patents and Trademarks